(12) United States Patent
Crawford et al.

(10) Patent No.: US 7,604,613 B2
(45) Date of Patent: Oct. 20, 2009

(54) SYRINGE HAVING A RETRACTABLE NEEDLE

(75) Inventors: Jamie Crawford, New York, NY (US); Frank Francavilla, Branchville, NJ (US); Roger Groskopf, Saddle Brook, NJ (US)

(73) Assignee: Beckton, Dickinson and Company, Franklin Lakes, NJ (US)

( * ) Notice: Subject to any disclaimer, the term of this patent is extended or adjusted under 35 U.S.C. 154(b) by 214 days.

(21) Appl. No.: 10/760,733

(22) Filed: Jan. 20, 2004

(65) Prior Publication Data
US 2005/0159705 A1 Jul. 21, 2005

(51) Int. Cl.
*A61M 5/00* (2006.01)
(52) U.S. Cl. .................... 604/110; 604/195; 604/187; 604/198
(58) Field of Classification Search ............ 604/110, 604/187, 263, 111–117, 192–198
See application file for complete search history.

(56) References Cited

U.S. PATENT DOCUMENTS

| | | | |
|---|---|---|---|
| 4,573,976 A | 3/1986 | Sampson | |
| 4,631,057 A | 12/1986 | Mitchell | |
| 4,737,144 A | 4/1988 | Choksi | |
| 4,747,831 A | 5/1988 | Kulli | |
| 4,795,432 A | 1/1989 | Karczmer | |
| 4,813,940 A | 3/1989 | Parry | |
| 4,985,021 A | 1/1991 | Straw | |
| 4,998,920 A | 3/1991 | Johnson | |
| 5,026,356 A | 6/1991 | Smith | |
| 5,053,010 A * | 10/1991 | McGary et al. ............ | 604/110 |
| 5,053,018 A | 10/1991 | Talonn | |
| 5,061,251 A | 10/1991 | Juhasz | |
| 5,151,088 A | 9/1992 | Allison | |
| 5,156,599 A | 10/1992 | Ranford | |

(Continued)

FOREIGN PATENT DOCUMENTS

EP 0 307 367 A1 6/1992

(Continued)

*Primary Examiner*—Kevin C Sirmons
*Assistant Examiner*—Phillip Gray
(74) *Attorney, Agent, or Firm*—David M. Fortunato; Cohen Pontani Lieberman & Pavane LLP

(57) ABSTRACT

A medical device for delivering a medicament to a patient. The device includes a syringe barrel with a plunger having a hollow front end and a stopper positioned over the plunger front end to seal the plunger front end. The stopper is movably inserted in the barrel to expel medicament in the barrel. A needle cannula is fixed to a needle cannula hub and is movable between an initial position in which the forward tip of the needle cannula is exposed and a retracted position in which the forward tip is contained within the medical device. A plug seal releasably secures the needle cannula hub to an end of the barrel, and a hub adapter secures the plug seal to the barrel end. A cutter positioned on the plunger pierces the stopper when the stopper is pressed against the plug seal to open the hollow front end of the plunger. The plunger also engages the plug seal to allow the needle cannula hub to move, via an urging member, to the retracted position through the front end of the plunger.

29 Claims, 6 Drawing Sheets

U.S. PATENT DOCUMENTS

| | | | |
|---|---|---|---|
| 5,163,918 A | 11/1992 | Righi | |
| 5,193,552 A | 3/1993 | Columbus | |
| 5,197,953 A | 3/1993 | Colonna | |
| 5,201,708 A | 4/1993 | Martin | |
| 5,217,437 A | 6/1993 | Talonn | |
| 5,242,420 A | 9/1993 | Martin | |
| 5,246,427 A | 9/1993 | Sturman | |
| 5,300,040 A | 4/1994 | Martin | |
| 5,304,149 A | 4/1994 | Morigi | |
| 5,308,332 A | 5/1994 | Dillard, III | |
| 5,312,372 A | 5/1994 | DeHarde et al. | |
| 5,336,176 A | 8/1994 | Yoon | |
| 5,342,309 A | 8/1994 | Hausser | |
| 5,342,320 A | 8/1994 | Cameron | |
| 5,370,628 A | 12/1994 | Allison | |
| 5,385,551 A * | 1/1995 | Shaw | 604/110 |
| 5,385,555 A | 1/1995 | Hausser | |
| 5,389,085 A | 2/1995 | D'Alessio | |
| 5,417,660 A | 5/1995 | Martin | |
| 5,562,626 A | 10/1996 | Sanpietro | |
| 5,578,011 A * | 11/1996 | Shaw | 604/110 |
| 5,651,774 A | 7/1997 | Taranto | |
| 5,658,254 A | 8/1997 | Reichenbach | |
| 5,681,292 A | 10/1997 | Tober | |
| 5,713,871 A | 2/1998 | Stock | |
| 5,735,823 A | 4/1998 | Berger | |
| 5,769,822 A * | 6/1998 | McGary et al. | 604/110 |
| 5,800,395 A | 9/1998 | Botich | |
| 5,800,403 A * | 9/1998 | Pressly et al. | 604/195 |
| 5,882,342 A | 3/1999 | Cooper | |
| 5,935,104 A | 8/1999 | Janek et al. | |
| 5,961,491 A * | 10/1999 | McGary et al. | 604/110 |
| 6,017,329 A | 1/2000 | Hake | |
| 6,077,253 A | 6/2000 | Cosme | |
| 6,162,197 A | 12/2000 | Mohammad | |
| 6,228,054 B1 | 5/2001 | Dysarz | |
| 6,319,233 B1 | 11/2001 | Jansen | |
| 6,409,701 B1 | 6/2002 | Cohn et al. | |
| 6,432,087 B1 | 8/2002 | Hoeck et al. | |
| 6,432,088 B1 | 8/2002 | Huang et al. | |
| 6,440,104 B1 | 8/2002 | Newby et al. | |
| 6,443,929 B1 | 9/2002 | Kuracina | |
| 6,458,101 B1 | 10/2002 | Hu | |
| 6,458,105 B1 | 10/2002 | Rippstein et al. | |
| 6,461,333 B1 | 10/2002 | Frezza | |
| 6,461,362 B1 | 10/2002 | Halseth | |
| 6,475,194 B2 | 11/2002 | Domici, Jr. | |
| 6,478,780 B1 | 11/2002 | Shields | |
| 6,494,863 B1 | 12/2002 | Shaw | |
| 6,511,460 B1 | 1/2003 | Arnissolle | |
| 6,514,229 B1 | 2/2003 | Huang | |
| 6,527,742 B1 | 3/2003 | Malenchek | |
| 6,530,903 B2 | 3/2003 | Wang | |
| 6,547,762 B1 | 4/2003 | Botich | |
| 6,558,357 B1 | 5/2003 | Hoeck | |
| 6,565,540 B1 | 5/2003 | Perouse | |
| 6,569,115 B1 | 5/2003 | Barker | |
| 6,569,124 B1 | 5/2003 | Perouse | |
| 6,589,209 B1 | 7/2003 | Dysarz | |
| 6,595,954 B1 | 7/2003 | Luther | |
| 6,605,073 B1 | 8/2003 | Pressly | |
| 2002/0065488 A1 | 5/2002 | Suzuki et al. | |
| 2002/0193737 A1 | 12/2002 | Popovsky | |
| 2002/0193746 A1 | 12/2002 | Chevallier | |
| 2002/0193747 A1 | 12/2002 | Denolly | |
| 2003/0023205 A1 | 1/2003 | Botich | |
| 2003/0028171 A1 | 2/2003 | DeHarde | |
| 2003/0036730 A1 | 2/2003 | Von Teichert | |
| 2003/0050601 A1 | 3/2003 | Righi | |
| 2003/0050607 A1 | 3/2003 | Gaagnieux | |
| 2003/0078546 A1 | 4/2003 | Jensen | |
| 2003/0083627 A1 | 5/2003 | Chen | |
| 2003/0114799 A1 | 6/2003 | Cheikh | |
| 2003/0144630 A1 | 7/2003 | Chang | |
| 2003/0149403 A1 | 8/2003 | Barker | |
| 2003/0149404 A1 | 8/2003 | Lehmann | |

FOREIGN PATENT DOCUMENTS

| | | |
|---|---|---|
| EP | 0 680 767 A1 | 11/1995 |
| EP | 0 864 335 A2 | 9/1996 |
| EP | 0 740 942 A1 | 11/1996 |
| EP | 0 966 983 A1 | 12/1999 |
| EP | 1 258 263 A1 | 11/2002 |
| EP | 1 260 242 A1 | 11/2002 |
| EP | 0 901 391 B1 | 1/2003 |
| EP | 0 963 213 B1 | 1/2003 |
| EP | 1 273 316 A1 | 1/2003 |
| EP | 1 281 410 A1 | 2/2003 |
| EP | 0 916 354 B1 | 3/2003 |
| EP | 1 287 842 A1 | 3/2003 |
| EP | 1 291 029 A1 | 3/2003 |
| EP | 1 291 030 A1 | 3/2003 |
| EP | 1 317 938 A1 | 6/2003 |
| EP | 0 984 804 B1 | 7/2003 |
| EP | 1 329 234 A2 | 7/2003 |
| EP | 0 941 134 B1 | 8/2003 |
| EP | 1 205 173 A2 | 9/2003 |
| EP | 1 205 173 A3 | 9/2003 |
| EP | 0 734 738 B1 | 10/2003 |
| EP | 1 049 503 B1 | 10/2003 |
| FR | 2 830 764 A1 | 4/2003 |
| FR | 2 830 765 A1 | 4/2003 |
| JP | 2001193714 | 12/2002 |
| WO | WO 01/41841 A2 | 6/2001 |
| WO | WO 01/41841 A3 | 6/2001 |
| WO | WO 01/60435 A1 | 8/2001 |
| WO | WO 01/85238 A2 | 11/2001 |
| WO | WO 02/089878 A1 | 11/2002 |
| WO | WO 02/098480 A2 | 12/2002 |
| WO | WO 02/098494 A2 | 12/2002 |
| WO | WO 02/098494 A3 | 12/2002 |
| WO | WO 03/000322 A1 | 1/2003 |
| WO | WO 03/000323 A1 | 1/2003 |
| WO | WO 03/011378 A1 | 2/2003 |
| WO | WO 03/015852 A1 | 2/2003 |
| WO | WO 03/022335 A2 | 3/2003 |
| WO | WO 03/033059 A1 | 4/2003 |
| WO | WO 03/033060 A1 | 4/2003 |
| WO | WO 03/041766 A2 | 5/2003 |
| WO | WO 03/045476 A1 | 6/2003 |
| WO | WO 03/045480 A1 | 6/2003 |
| WO | WO 03/045481 A1 | 6/2003 |
| WO | WO 03/063934 A1 | 8/2003 |
| WO | WO 03/068297 A1 | 8/2003 |
| WO | WO 03/068298 A1 | 8/2003 |

* cited by examiner

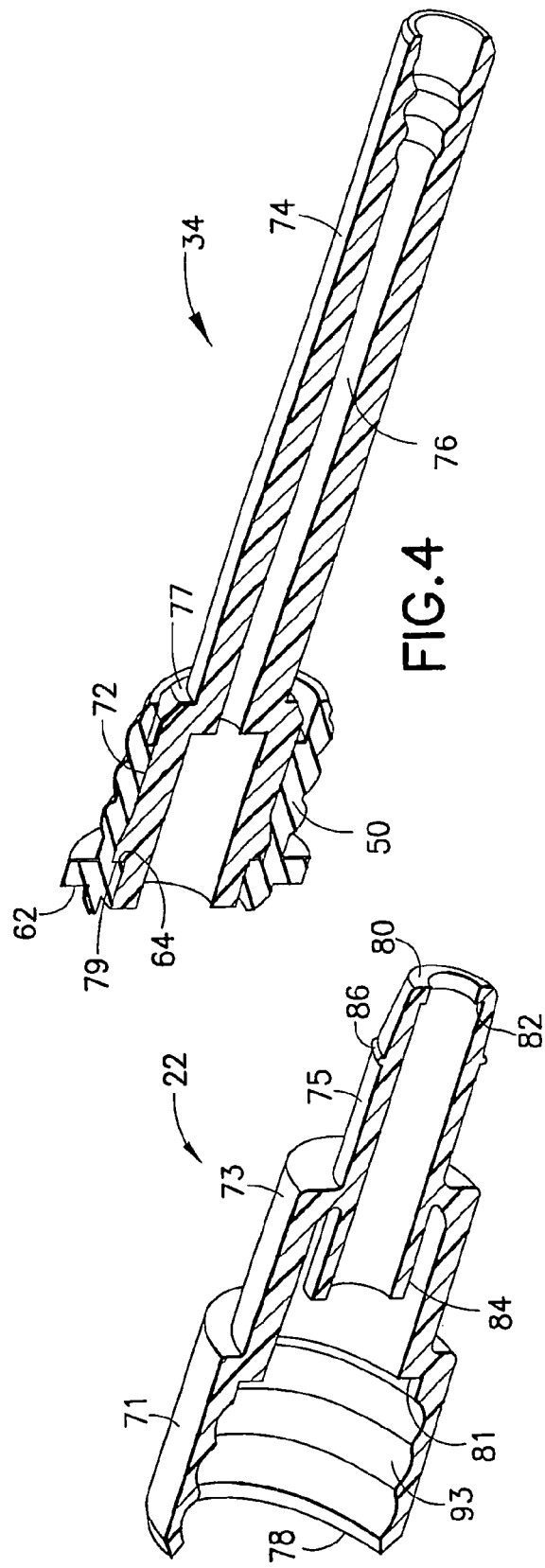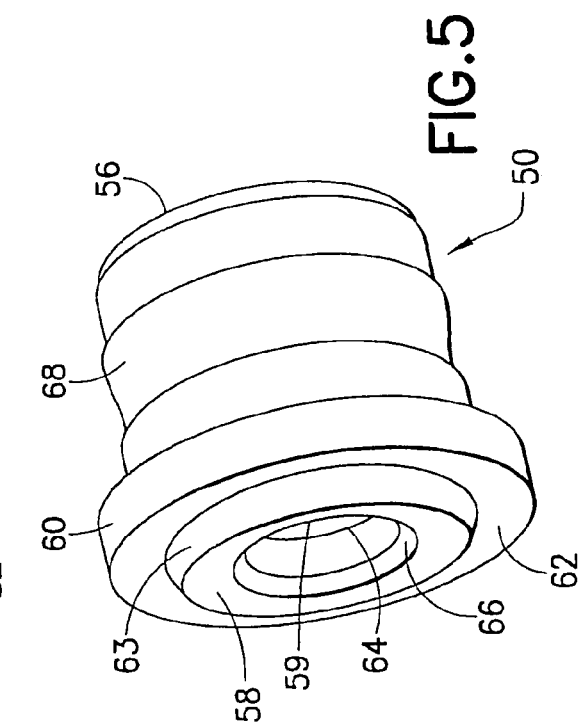

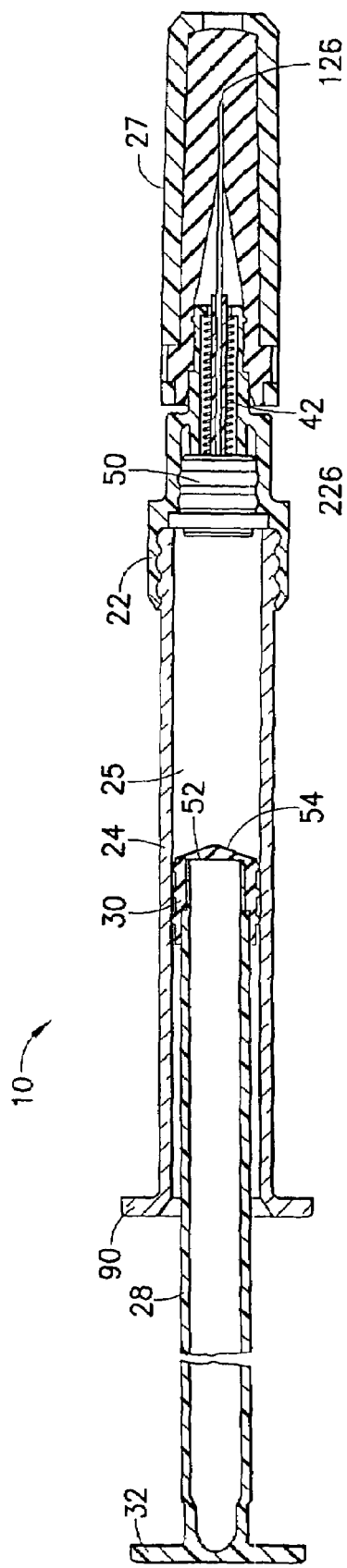
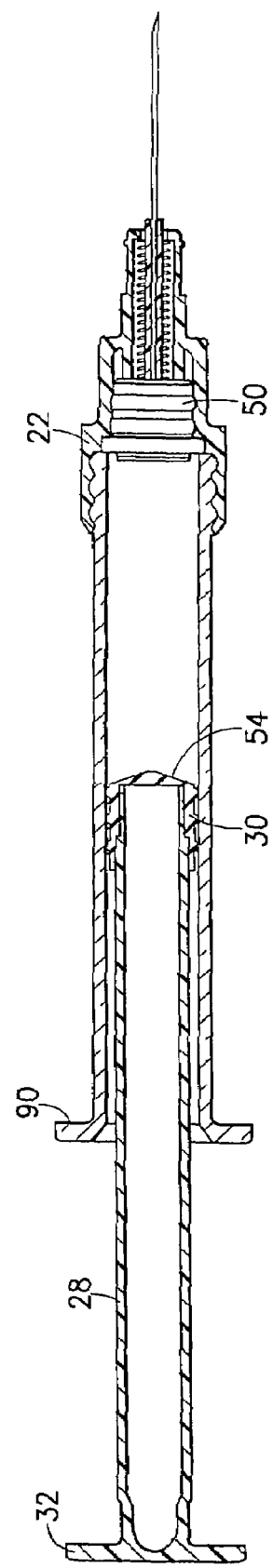
FIG.6
FIG.7

SYRINGE HAVING A RETRACTABLE NEEDLE

BACKGROUND OF THE INVENTION

1. Field of the Invention

The present invention relates to a medical device for delivering a dose of medicament by injection. More particularly, the present invention is directed to a syringe assembly having a mechanism for retracting the needle into the syringe barrel after use to prevent accidental needle sticks.

2. Description of the Related Art

Syringes used for the delivery of medicaments to patients are well known. Oftentimes syringes are prefilled with a dosage of a medicament or other substance by a pharmaceutical manufacturer and then distributed to end users such as health care professionals or patients for administration of the prefilled medicament. Such syringes typically include a cylindrical hollow barrel which may be formed of a glass or plastic material and which includes the medicament. One end of the barrel is fitted with a fixed or removable hollow needle, and the other end of the barrel receives a plunger having a stopper which is slidable with respect to the barrel for delivery of the medicament to the hollow needle, i.e., to urge the medicament toward and out of the needle. A syringe assembly, which typically includes the above-described components, is usually stored with a removable needle cover which protects the needle from damage during storage and handling. Prior to use, the needle cover is removed to expose the needle.

To prevent a syringe user and, in particular, a health care professional from inadvertent sticks by the needle after use of the syringe on a patient, the syringe assembly may incorporate a safety shield which forms a guard to cover the needle after use. Certain attributes to be considered in such syringe assemblies are that the shield should be intuitive and easy to use, should preferably provide consistent and reliable activation, and should be operable with one hand. Other attributes are that such syringe assemblies require no change in current medicament delivery techniques, allow for dose adjustment, are preferably autoclavable, and allow for the inspection of contents before and after activation of the shield. Moreover, the use of the shield must not detrimentally affect processing and filling of the syringe at the pharmaceutical company, the assembly (i.e., syringe assembly and safety shield) must be easy to manufacture, must prevent accidental activation, and must limit the possibility of incurring cosmetic or structural damages.

SUMMARY OF THE INVENTION

The present invention relates to a medical device including a syringe barrel assembly with a retractable needle cannula supported by a needle cannula hub. The needle cannula and needle cannula hub are retracted upon full delivery of the medicament dosage in the syringe.

The medical device includes a barrel having a forward end and a rear end and which defines a reservoir within which the medicament may be contained. A needle cannula having a forward tip and a rear end is mounted, at its rear end, to a needle cannula hub for providing fluid communication of the needle cannula with the reservoir. The needle cannula hub is selectively movable between an initial position in which the forward tip of the needle cannula is exposed, and a retracted position in which the forward tip of the needle cannula is disposed in the medical device. A barrel hub member is coupled to the forward end of the barrel over the needle cannula hub and is dimensioned to provide retractable telescoping movement of the needle cannula hub with respect to the barrel hub member to allow the needle cannula hub to move to the retracted position. A retaining member is seated between the forward end of the barrel and the barrel hub member for releasably securing the needle cannula hub at the barrel forward end when the needle cannula hub is in the initial position. An urging member is provided in contact with the needle cannula hub and the barrel hub for exerting a force to bias the needle cannula hub from the initial position to the retracted position. A plunger rod having a hollow first end bounded by an edge and supporting a stopper is positioned in the reservoir. The plunger rod has a second end having a thumb pad for receiving medicament delivery pressure for causing the plunger to move within the reservoir to cause the medicament to be expelled from the reservoir. The plunger edge is configured for piercing the stopper when the stopper is fully inserted into the barrel and for interacting with the retaining member to release the needle cannula hub from the retaining member. This allows the needle cannula hub to move, by the urging member, to the retracted position through the hollow front end of the plunger rod.

In one embodiment, the retaining member is cylindrically-shaped and has a forward face and a rear end defining a bore. The forward face is dimensioned for seating at the forward end of the barrel.

In another embodiment, the retaining member comprises a flange proximate the forward face of the retaining member for seating between the barrel forward end and the barrel hub member. A seat is defined on an inner wall of the retaining member which bounds the bore for providing releasable securement of the needle cannula hub to the retaining member.

In another embodiment, the plunger rod forward end pierces the front face of the stopper and also acts directly on the retaining member to release the needle cannula hub from the retaining member to allow the needle cannula hub to move to the retracted position.

In another embodiment, the urging member is a coil spring which is arranged on the needle cannula hub and contacts the needle cannula hub and the barrel hub member for urging the needle cannula hub to the retracted position.

In another embodiment, the plunger rod is aligned with the bore formed in the retaining member for radially expanding the bore when the first end of the plunger is pressed into the bore, for releasing the needle cannula hub from the retaining member.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference characters denote similar elements throughout the several views:

FIG. 3 is an enlarged cross-sectional view of a hub adapter component of the medical device of FIG. 1;

FIG. 4 is an enlarged cross-sectional view of a needle hub component and a plug seal of the medical device of FIG. 1;

FIG. 5 is an enlarged perspective view of a plug seal component of the medical device of FIG. 1;

FIG. 6 is a cross-sectional view of an assembled medical device of FIG. 1;

FIG. 7 is a cross-sectional view of the medical device of FIG. 6, with a needle shield removed;

DETAILED DESCRIPTION OF THE PRESENTLY PREFERRED EMBODIMENTS

Figure 1:
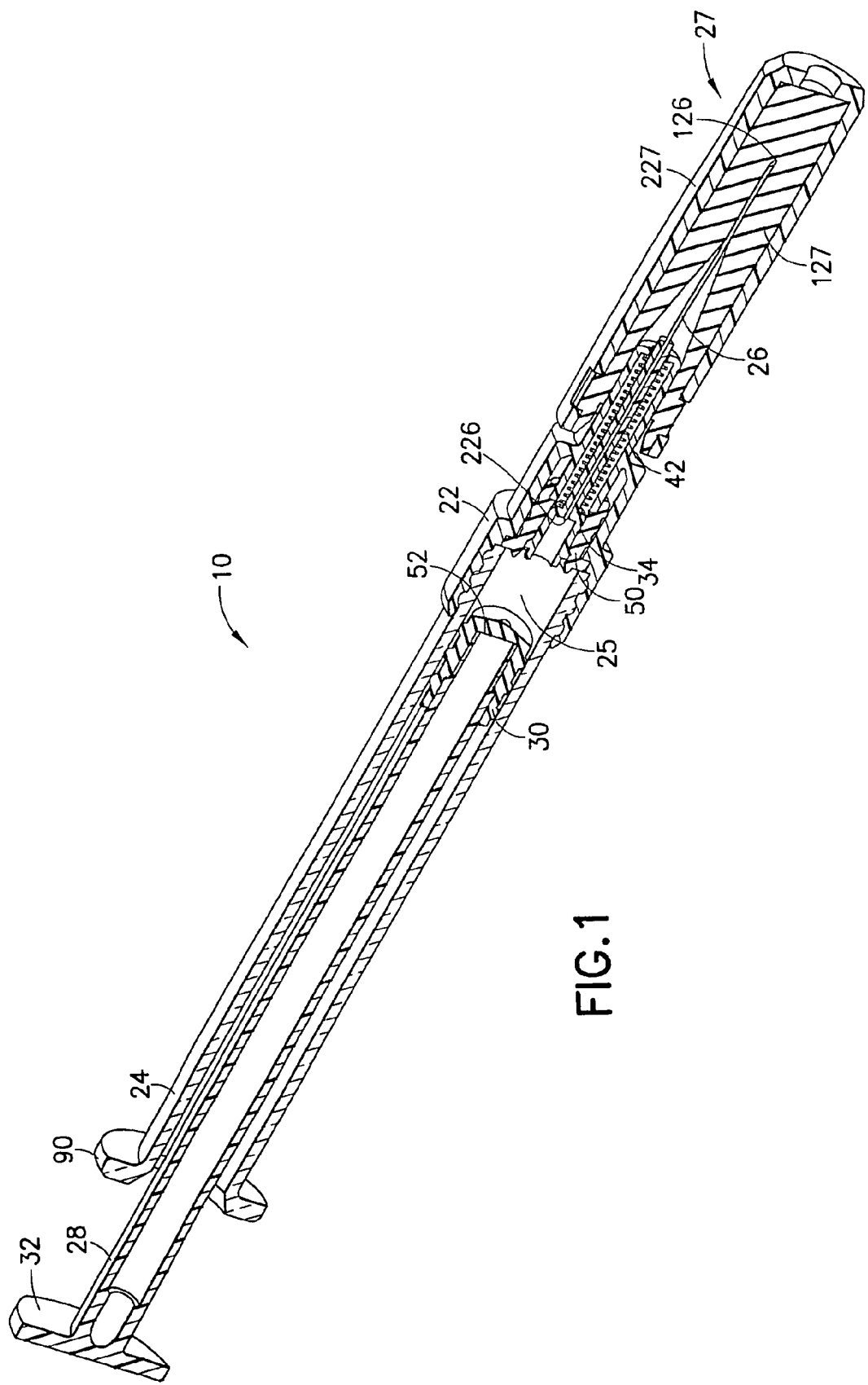
FIG. 1 is a longitudinal sectional view of a medical device according to an embodiment of the present invention.
Figure 2:
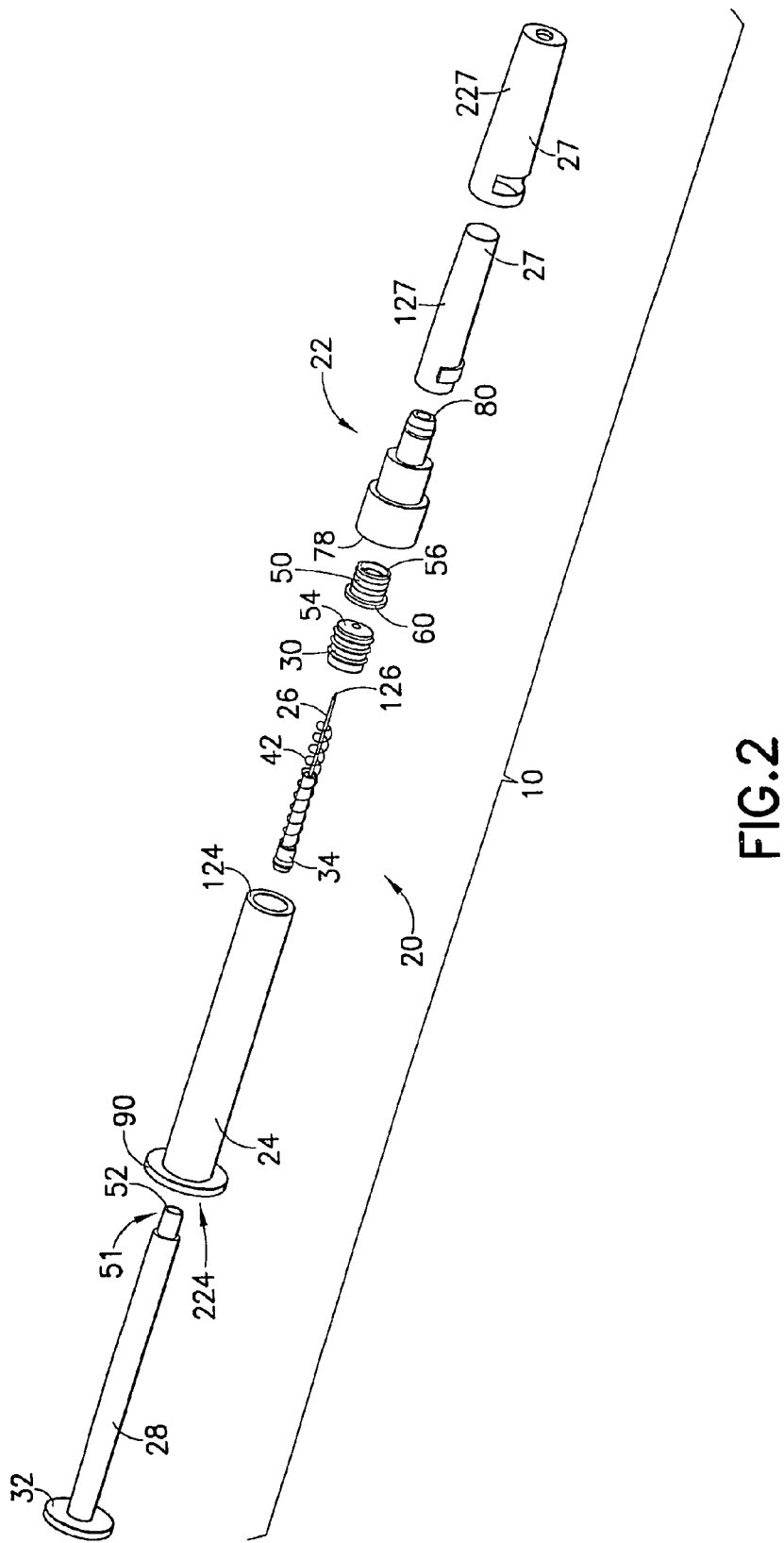
FIG. 2 is an exploded view of the medical device of FIG. 1.

FIGS. 1 and 2 show a medical device 10 for delivery of a medicament into a patient constructed in accordance with an embodiment of the present invention. As used herein the term "medicament" is intended to refer to any drug substance, vaccine, or other substance that is injected into a patient.

Figure 8:
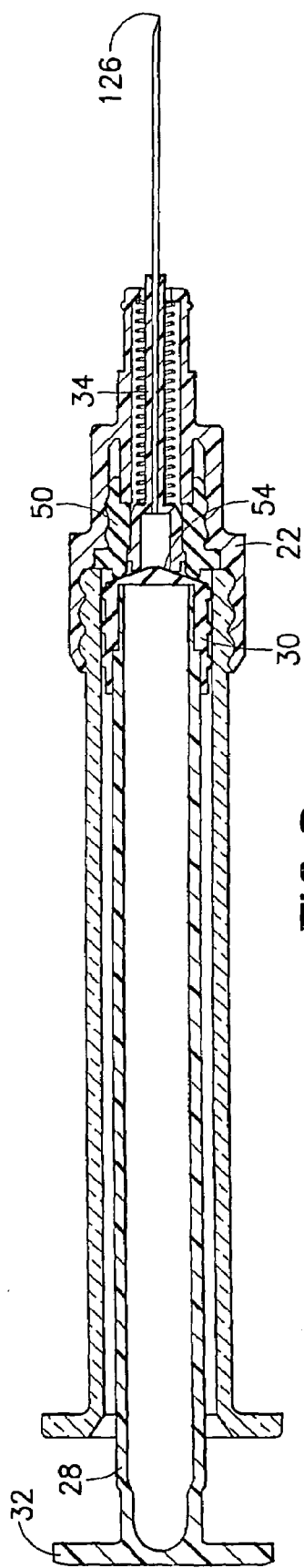
FIG. 8 is a cross-sectional view of the medical device of FIG. 7 after delivery of a medicament.
Figure 9:
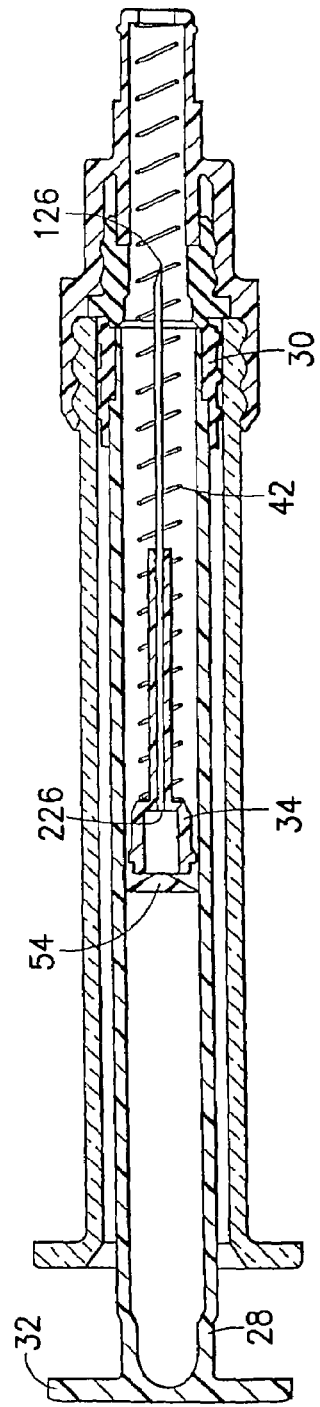
FIG. 9 is a cross-sectional view of the medical device of FIG. 7 after the needle is moved to a retracted position.

The medical device 10 includes a syringe barrel 24 having a front end 124 and a rear end 224. The barrel 24 is preferably made of molded plastic. Alternatively, the barrel 24 may be formed from glass. The barrel 24 defines a reservoir 25 within which the medicament may be held prior to the use of the medical device 10. A needle cannula 26 having a forward tip 126 and a rearward end 226 is mounted in a needle cannula hub 34 proximate the front end 124 of the barrel 24. The needle cannula 26 is permanently connected to the needle cannula hub using an adhesive, glue, friction fit or other known or hereafter developed material or technique. The rear end 226 of the needle cannula is in fluid communication with the reservoir 25 in the position shown in FIG. 1. The needle cannula hub 34 is arranged at, and movably mounted to, the front end 124 of the barrel 24 by a plug seal retaining member 50 and a barrel hub member or hub adapter 22, as more fully described below. The mounting of the needle cannula hub 34 to the plug seal 50 allows the needle cannula hub 34, with the needle cannula 26 connected thereto, to move from an initial position shown in FIG. 8 wherein the forward tip 126 of the needle cannula 26 extends beyond the front end of hub adapter 22, to a retracted position in which the forward tip 126 of the needle cannula 26 is contained within the device 10 as shown in FIG. 9.

A plunger or plunger rod 28 has a front end 51 which is disposed in the barrel 24. The plunger rod may be formed of plastic or other known moldable material and is configured as a hollow tube. Alternatively, the plunger rod 28 may include a hollow portion proximate the front end 51. A stopper or piston 30 having a front face 54 that is preferably made of a relatively thin rubber material is arranged on the front end 51 of the plunger rod 28 and is movable with the plunger rod 28 within the barrel 24. The front end 51 of the plunger rod is configured as, or surrounded by, a cutting edge 52 which may be integrally formed with the plunger rod 28 or separately formed and affixed to the front end of the plunger rod 28. The cutting edge 52 interacts with and pierces the front face 54 of the stopper 30 as the front face is pressed or clamped between the cutting edge 52 and the plug seal 50, which occurs at the completion of a medicament delivery stroke as explained below. A second end of the plunger rod 28 includes a thumb press area or thumb pad 32 used for receiving pressure from the user's thumb for moving the piston 30 into and within the barrel 24 for urging the medicament in the reservoir 25 into the needle cannula 26.

As further shown in FIGS. 1 and 3, a removable needle shield 27 is disposed over the hub adapter 22 and forms a snap fit with a radial flange 86. The needle shield 27 protects the needle from damage during handling of the medical device prior to its intended use, and also protects users of the device from accidental needle sticks. Instead of a snap fit, a luer type connection may be provided to releasably secure the removable needle shield 27 to the hub adapter 22. Prior to use of the medical device 10, the needle shield 27 is removed. As is known, the needle shield may include a pliable part 127 and a rigid part 227.

As shown most clearly in FIGS. 2 and 3, the hub adapter 22 includes three cylindrical sections 71, 73, 75, defined between a rear end 78 and a front end 80. The cylindrical sections have different diameters including a larger diameter for section 71, an intermediate diameter for section 73, and a smaller diameter for section 75. An annular ridge or shelf 81 is formed between the sections 71, 73. A flange 82 is formed at the forward end 80 of the hub adapter 22. Extending from the small cylindrical section 75 is a collar which functions as an anchor or seat 84 for engagement with the plug seal 50, as explained below. Detailing 93 formed on the inner surfaces of the large cylindrical section 71 and intermediate cylindrical section 73 are provided for affixing the hub adapter 22 to the front end 124 of the barrel and to the plug seal 50, respectively. The hub adapter is preferably formed of a moldable material, such as plastic.

The plug seal 50 is preferably formed from a moldable and elastic material, such as rubber, and is mounted in the hub adapter 22 and positioned at the barrel front end 124. As shown in FIG. 5, the plug seal is generally cylindrically-shaped and dimensioned to seat within the hub adapter 22 and to provide coupling to the front end 124 of the barrel 24. The plug seal 50 includes a forward end 56 and a rear end 58 through which a central bore 59 is formed for communicating the medicament contained in the reservoir 25 to the needle cannula 26. A substantially radial flange 60 is located on the plug seal 50 proximate the rear end 58 but axially offset therefrom to provide a barrel seat surface 62. An axial portion 63 is defined between the flange 60 and the rear end 58 and dimensioned to seat at the barrel front end 124. A needle hub seat 64, in the form of a ridge or groove or channel (shown in FIG. 4) is formed on the inner surface of the plug seal proximate the flange 60 to provide an anchor for the needle hub 34. An inner surrounding wall of the axial portion 63 is provided with an angled release surface 66 which is used to radially stretch the central bore 59 when engaged with the front end 51 of the plunger rod 28 for allowing the needle cannula hub 34 to move to its retracted position. Surface details 68 are also provided on the outer wall of the plug seal to provide a secure engagement between the plug seal and hub adapter 22. When the plug seal 50 is positioned in the large cylindrical portion 71 of the hub adapter, the flange 60 rests on the annular shelf 81.

As shown in FIG. 4, the needle hub 34 includes a short, hollow cylindrical section 72 in communication with an elongated, hollow cylindrical section 74 having a passageway 76 formed therein. A biasing seat 77 is formed between the cylindrical sections 72, 74, and a notch 79 is formed at the free end of the short cylindrical section for mating with or otherwise contacting the needle hub seat 64 on the plug seal 50 when the needle hub is inserted into the plug seal bore 59 in the intended manner. The needle hub 34 can be integrally formed from any moldable and resilient material, such as plastic. Alternatively, the short and elongated cylindrical sections 72, 74 can be formed separately from the same or different materials and then attached to each other, such as by an adhesive, etc.

As most clearly shown in FIG. 1, when the medical device 10 is assembled in its intended manner, the short cylinder section 72 of the needle hub 70 is positioned within the central bore 59 of the plug seal 50 so that the plug seal seat 79 rests on needle hub seat 64. The hub adapter 22 is positioned at the forward end 124 of the barrel 24 and over the needle hub 34 and plug seal 50 so that the plug seal seats in the large cylindrical section 71 and the flange 60 is clamped between the front end 124 of the barrel and the annular shelf 81. The large cylindrical portion is dimensioned for this purpose to form a friction fit with the front end 124 of the barrel. Alternatively, ridges 93 may mate with or otherwise engage like ridges formed at the front end of the barrel 24. When so-arranged, the elongated cylindrical section 74 with the needle cannula 26 connected thereto is slidably positioned in the small cylindrical section 75 of the hub adapter 22 so that the needle cannula forward tip 126 extends from beyond the second end 80.

Figure 10:
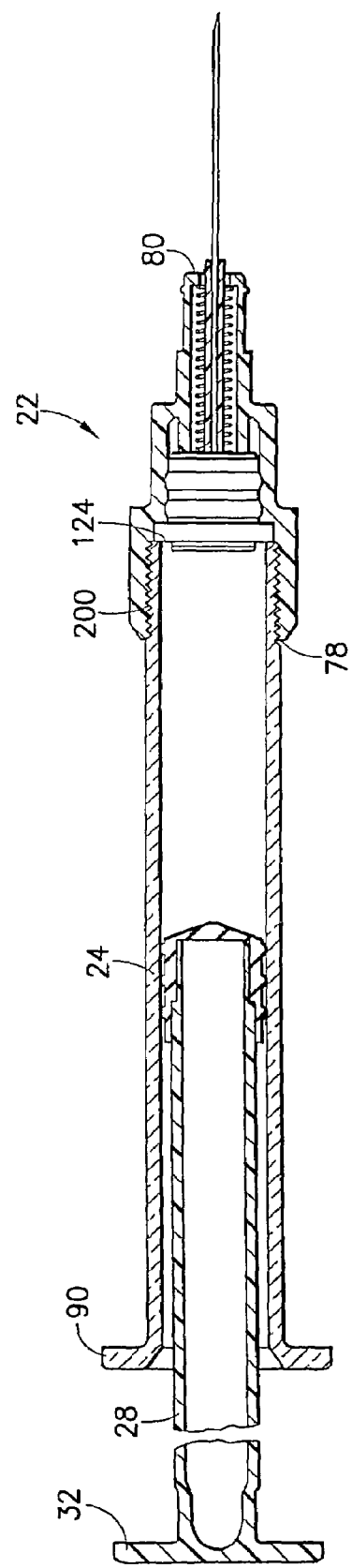
FIG. 10 is a cross-sectional view of another embodiment of the present invention.

As an alternative to a friction fit between the hub adapter 22 and the front end 124 of the barrel 24, the barrel may be configured with threading 200 (as shown in FIG. 10) formed at the front end 124 for engaging threading the hub adapter 22. As a further alternative, or in addition to a friction fit or threading, adhesive may be used to secure the hub adapter 22 to the barrel front end 124.

An urging member 42 is arranged between the needle cannula hub 34 and the hub adapter 22 for urging the needle cannula hub 34 in the direction of the rear end 224 of the barrel 24. In a preferred embodiment, a coil spring 42 is used and is dimensioned to facilitate insertion of the long cylindrical section 74 of the needle hub 34 such that one end of the spring contacts urging member seat 77 on the needle hub, and another end of the spring contacts flange 82 on the hub adapter 22. When in this position, the spring 42 is compressed or charged between the needle hub 34 and the hub adapter 22 to bias the needle hub 34 in a direction toward the rear end 224 of the barrel 24 during activation or release from the plug seal 50. As an alternative to a coil spring, a biasing arm or other force exerting member may be employed for this purpose.

With reference to FIGS. 1 and 2, the plunger rod front end 51 and, specifically, the cutting edge 52, is aligned with the central bore 59 and dimensioned to tightly engage the release surface 66 of the plug seal 50. This occurs at the completion of a medicament delivery stroke when the front end 51 of the plunger rod 28 is proximate the plug seal 50. At this point, the piston 30 is clamped between the release surface 66 and the front cutter edge 52 of the plunger rod 28. This is shown in FIG. 8. Additional pressure applied to the thumb pad 32 will cause the front edge 52 to cut through a portion of the front face 54 of the piston 30. Continued pressure to the thumb pad will also engage the forward end 51 of the plunger rod 28 with the release surface 66. Due to the elasticity of the plug seal 50 and the orientation of the release surface 66, such continued pressure causes the central bore 59 to expand, whereupon the plug seal seat 79 on the needle hub 34 will disengage from the needle hub seat 64 on the plug seal 50. Once this occurs, clearance is provided to allow the needle hub 34, with the needle cannula 26 connected thereto, to move under the urgency of spring 42 to the retracted position. Specifically, because the front end 51 of the plunger rod 28 is now open due to the cutting away of a portion of the front face 54 of the piston 30, the needle cannula 26 and the needle hub 34, along with the now-cut away portion of the front face 54, are forced into the retracted position, as shown in FIG. 9, within the open front end 51 of the plunger rod 28. When in the retracted position, the forward tip 126 of the needle cannula no longer extends beyond the hub adapter 22, thereby prohibiting a user of the medical device from contacting the forward tip 126. It is preferred that the additional pressure to the thumb pad 32 to cause cutting of the front face 54, expanding the plug seal 50, and thereby allow the needle hub 34 to move to the retracted position be applied upon removal of the needle cannula forward tip 126 from the patient. However, the additional pressure could, alternatively, be applied while the needle cannula remains in the patient.

A description of an exemplary usage of a preferred embodiment of the medical device 10 will now be provided with reference to FIGS. 6-9. It should be understood by a person of ordinary skill in the art that the following description is provided as an illustrative and non-limiting example. The health care professional receives the inventive medical device 10 prefilled with a desired single dosage of a medicament. Immediately prior to use, the needle shield 27 is removed and the needle cannula 26 (with the forward tip 126) is exposed. At this point, the needle hub 34 and needle cannula 26 are in the initial position as shown in FIG. 7. The health care professional pierces the patient's skin with the forward tip 126 of the needle cannula 26 and depresses the thumb pad 32 to cause the plunger rod 28 and piston 30 to move within the reservoir 25. As the plunger rod 28 and piston are moved into the reservoir, medicament is caused to be expelled from the reservoir through the plug seal 50, needle hub 34 and needle cannula 26, and into the patient. When the medicament is completely expelled from the reservoir so that the dose has been completely administered to a patient, the needle is removed from the patient and the additional pressure is applied to the plunger rod 28, i.e., to the thumb pad 32. In a preferred embodiment, details (not shown) on the barrel 24 engage the plunger rod 28 or thumb pad 32 to secure the plunger rod in the barrel, and prevent removal therefrom, when the plunger rod is fully inserted into the barrel.

The application of additional pressure to the plunger rod 28 causes the piston 30 to interact with the plug seal 50, which causes the piston to be clamped between the release surface 66 of the plug seal 50 and the front cutting end 52 of the plunger rod whereupon a portion of the front face 54 of the piston 30 is cut away from the piston 30. Continued pressure applied to the plunger rod causes the front end 51 to engage the release surface 66 and expand the central bore 59. Once this occurs, the needle hub 34 will be disengaged from the plug seal 50 to allow the needle hub, with the needle cannula 26 mounted thereto, to move to the retracted position contained in the plunger rod 28 by the urgency of the urging member 42. This movement will also push the detached portion of the front face 54 in a direction toward the thumb pad 32 as shown in FIG. 9. When in the retracted position, the forward tip 126 of the needle cannula 26 is no longer exposed as it is now contained within the hub adaptor 22 and/or the syringe barrel 24, with a portion, or all, of the needle cannula 28 contained within the plunger rod 28. The used medical device 10 may then be disposed of in a suitable sharps disposal container.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A medical device for delivering a medicament to a patient, comprising:
   a barrel having a forward end and a rear end and defining a reservoir within which the medicament may be contained;
   a needle cannula having a forward tip and a rear end;
   a needle cannula hub connected to said rear end of said needle cannula and providing fluid communication of said needle cannula with said reservoir, said needle cannula hub being selectively movable between an initial position in which said forward tip of said needle cannula is exposed, and a retracted position in which said forward tip of said needle cannula is disposed in said device;
   a barrel hub member coupled to said forward end of said barrel over said needle cannula hub and dimensioned to provide retractable telescoping movement of said needle cannula hub with respect to said barrel hub member to allow said needle cannula hub to move to said retracted position;
   a retaining member seated between said forward end of said barrel and said barrel hub member for releasably securing said needle cannula hub at said barrel forward end when said needle cannula hub is in said initial position, said retaining member having a forward face and rear end defining a bore therethrough, said forward face dimensioned for seating at said barrel forward end;
   an urging member in contact with said needle cannula hub and said barrel hub for exerting a force to bias said needle cannula hub from said initial position to said retracted position; and
   a plunger rod having a hollow first end bounded by a cutting edge and supporting a stopper and positioned in said reservoir, and a second end having a thumb pad for receiving medicament delivery pressure for causing said plunger rod to move within said reservoir to cause the medicament to be expelled from said reservoir, said plunger rod cutting edge configured for cutting away a portion of said stopper when said stopper is fully inserted into said barrel and for thereafter interacting with said retaining member to elastically radially expand the bore to a size sufficient to release said needle cannula hub from said retaining member and enable said needle cannula hub to move, by said urging member, to said retracted position though said hollow first end of said plunger rod.

2. The medical device of claim 1, wherein said retaining member comprises a flange proximate said forward face for seating between said barrel forward end and said barrel hub member, and a seat defined on an inner wall of said retaining member bounding said bore for providing releasable securement of said needle cannula hub to said retaining member.

3. The medical device of claim 2, wherein said retaining member abuts a rear end of said needle cannula hub when said needle cannula hub is in said initial position.

4. The medical device of claim 3, wherein said plunger rod forward end acts directly on said retaining member to release said needle cannula hub.

5. The medical device of claim 2, wherein said urging member is arranged on said needle cannula hub and in contact with said needle cannula hub and said barrel hub member for urging said needle cannula hub to said retracted position.

6. The medical device of claim 1, wherein said retaining member is arranged to abut a rear end of said needle cannula hub when said needle cannula hub is in said initial position.

7. The medical device of claim 6, wherein said plunger rod is aligned with the bore in said retaining member for elastically radially expanding said bore when said first end of said plunger rod is pressed into said bore for releasing said needle cannula hub from said retaining member.

8. The medical device of claim 1, wherein said retaining member is arranged between said urging member and said needle cannula hub, thereby preventing an urgency of said urging member from acting on said needle cannula hub in the initial position.

9. The medical device of claim 8, wherein said barrel hub member forms a friction fit with said barrel forward end.

10. The medical device of claim 1, wherein said needle cannula hub comprises a first section having a first diameter for interfacing with said retaining member, and an elongated second section having a second diameter smaller than said first diameter, and further comprising a seat disposed between said first and second sections for coupling to an end of said urging member.

11. The medical device of claim 10, wherein said barrel hub member comprises a flange for coupling to another end of said urging member, said urging member applying an expansion force against said seat and said flange for urging said needle cannula hub to said second position.

12. The medical device of claim 1, wherein said barrel comprises plastic.

13. The medical device of claim 1, wherein said barrel comprises glass.

14. The medical device of claim 1, wherein barrel forward end comprises a forward portion and wherein said barrel rear end comprises a rear portion, said barrel having threading on said forward portion to provide coupling to said barrel hub member.

15. The medical device of claim 14, wherein said forward barrel portion comprises plastic and wherein said rear barrel portion comprises glass.

16. The medical device of claim 1, wherein said stopper includes a side surface interacting with an inner surface of said barrel and a front surface and wherein said plunger rod cutting edge is configured for cutting away said front surface from said stopper.

17. The medical device of claim 16, wherein said cutting edge is integrally formed with said plunger rod.

18. The medical device of claim 1, wherein said retaining member comprises an outer surface having a first form, and wherein said barrel hub member comprises an inner surface having a second form complimentary to said first form so that, said retaining member engages said barrel hub member to secure said retaining member to said barrel hub member.

19. The medical device of claim 1, wherein said urging member is a coil spring.

20. The medical device of claim 1, wherein said plunger rod comprises a plastic material.

21. A medical device for delivering a medicament to a patient, comprising:

a barrel having a forward end and a rear end and defining a reservoir within which the medicament may be contained;

a needle cannula having a forward tip and a rear end;

a needle cannula hub connected to said rear end of said needle cannula and providing fluid communication of said needle cannula with said reservoir, said needle cannula hub being selectively movable between an initial position in which said forward tip of said needle cannula is exposed, and a retracted position in which said forward tip of said needle cannula is disposed in said device;

a barrel hub member coupled to said forward end of said barrel over said needle cannula hub and dimensioned to provide retractable telescoping movement of said needle cannula hub with respect to said barrel hub member to allow said needle cannula hub to move to said retracted position;

means for releasably securing said needle cannula hub at said barrel forward end when said needle cannula hub is in said first position said releasably securing means comprising a retaining member having a forward face and a rear end defining a bore therethrough and positioned between said forward end of said barrel and said barrel hub member;

urging means disposed between said barrel hub member and said needle cannula hub for urging said needle cannula hub to said retracted position when said releasably securing means is activated; and a plunger rod having a hollow first end supporting a stopper and positioned in said reservoir, and a second end having a thumb pad for receiving medicament delivery pressure for causing said plunger rod to move within said reservoir to cause the medicament to be expelled from said reservoir, said plunger rod comprising cutting means for cutting away a portion of said stopper when said stopper is fully inserted into said barrel, said cutting means further comprising means for activating said releasably securing means after said stopper portion is cut away, said activating means comprising means for engaging said bore and elastically radially expanding said bore to a size sufficient to release said needle cannula hub from said releasably securing means, for allowing said urging means to move said needle cannula hub to said retracted position through said hollow first end of said plunger rod.

22. The medical device of claim 21, wherein said retaining member is cylindrically-shaped, said forward face dimensioned for seating at said barrel forward end.

23. The medical device of claim 22, wherein said retaining member comprises a flange proximate said forward face for seating between said barrel forward end and said barrel hub member, and a seat defined on an inner wall of said retaining member bounding said bore for providing releasable securement of said needle cannula hub to said retaining member.

24. The medical device of claim 23, wherein said retaining member abuts a rear end of said needle cannula hub when said needle cannula hub is in said initial position.

25. The medical device of claim 24, wherein said plunger rod forward end acts directly on said retaining member to release said needle cannula hub.

26. The medical device of claim 23, wherein said urging means is arranged on said needle cannula hub and in contact with said needle cannula hub and said barrel hub member for urging said needle cannula hub to said retracted position.

27. The medical device of claim 26, wherein said plunger rod is aligned with said bore for elastically radially expanding said bore when said first end of said plunger is pressed into said bore, for releasing said needle cannula hub from said retaining member.

28. The medical device of claim 21, wherein said stopper includes a side surface interacting with an inner surface of said barrel and a front surface and wherein said cutting means comprises a cutting edge mounted to said plunger rod first end for cutting away said front surface from said stopper.

29. The medical device of claim 28, wherein said cutting edge is integrally formed with said plunger rod.

* * * * *

UNITED STATES PATENT AND TRADEMARK OFFICE
CERTIFICATE OF CORRECTION

PATENT NO.        : 7,604,613 B2
APPLICATION NO. : 10/760733
DATED             : October 20, 2009
INVENTOR(S)       : Crawford et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 222 days.

Signed and Sealed this

Fifth Day of October, 2010

David J. Kappos
*Director of the United States Patent and Trademark Office*